United States Patent [19]
Krauter et al.

[11] Patent Number: 5,879,286
[45] Date of Patent: Mar. 9, 1999

[54] DIAGNOSTIC INSTRUMENT ILLUMINATION SYSTEM

[75] Inventors: Allan I. Krauter, Syracuse; Dale C. Saddlemire, Cortland, both of N.Y.

[73] Assignee: Welch Allyn, Inc., Skaneateles Falls, N.Y.

[21] Appl. No.: 748,374

[22] Filed: Nov. 13, 1996

[51] Int. Cl.$^6$ ........................................... A61B 1/06
[52] U.S. Cl. .................... 600/135; 600/172; 600/173; 600/175
[58] Field of Search ................. 600/109, 165, 600/129, 160, 172, 173, 176, 177, 171, 178, 189, 199, 200, 175; 359/376, 377, 385–390; 396/14, 16, 17, 19

[56] References Cited

U.S. PATENT DOCUMENTS

| | | |
|---|---|---|
| 2,144,653 | 1/1939 | Graff ........................................ 359/390 |
| 2,823,666 | 2/1958 | Hallpike et al. ......................... 600/129 |
| 3,127,115 | 3/1964 | Yellott et al. ............................ 600/178 |
| 4,621,283 | 11/1986 | Feinbloom ............................... 600/109 |
| 4,657,357 | 4/1987 | Nishimura et al. ...................... 359/377 |
| 4,690,522 | 9/1987 | Welsh ...................................... 359/390 |
| 4,797,736 | 1/1989 | Kloots et al. ............................ 600/109 |
| 5,469,294 | 11/1995 | Wilt et al. ................................ 359/385 |

*Primary Examiner*—John P. Leubecker
*Attorney, Agent, or Firm*—Wall Marjama Bilinski & Burr

[57] ABSTRACT

An illumination beam director for use with a diagnostic instrument having an optical lens system including a camera aperture for observing along an optical viewing axis passing through the camera aperture, and an illuminator including an illuminator aperture for projecting illumination along a first illumination axis passing through the illumination aperture. The light beam director includes a pair of opposed redirecting surfaces which receive the light from the illuminator along a first illumination axis and redirect the light onto a second illumination axis, wherein the second illumination axis is closer to the optical axis than is the first illumination axis to overcome shadowing effects on the viewing axis.

14 Claims, 5 Drawing Sheets

DIAGNOSTIC INSTRUMENT ILLUMINATION SYSTEM

FIELD OF THE INVENTION

This invention relates to diagnostic instruments, and more specifically to an improved off-axis illumination system for a colposcope for correcting shadowing effects induced during an examination procedure.

BACKGROUND OF THE INVENTION

Diagnostic instruments having viewing optics for viewing a target are commonly known, particularly in the medical field, for conducting diagnostic examinations. An example is a colposcope which is used by gynecologists to conduct patient vaginal examinations. Typically, the scope is placed a predetermined distance from the patient and pointed at a speculum, which is used to hold open the vaginal cavity in order to allow viewing of the cervix. Light from an illumination source of the colposcope is projected along an illumination axis with the illumination system being set at an angle off-axis relative to an optical viewing system, such as shown in FIG. 2.

A recurring problem is that the presence of the speculum, as well as the off-axis alignment of the illumination system causes shadowing of the image being viewed,( ie: the cervix or other intended target), making examination difficult, as well as time-consuming to perform. In the same described procedure, shadowing of the viewed image may also occur when a physician attempts to obtain a culture, or otherwise introduces a probe or swab into the vaginal cavity.

There is a need, therefore, to provide an improved illumination system, particularly for a colposcope, but advantageously for other diagnostic instruments as well, which reduces the effects of shadowing and allows more efficient use of the instrument's optical system.

SUMMARY OF THE INVENTION

It is therefore a primary object of the present invention to provide an improved illumination system, useful with many diagnostic instruments, but in particular with those using off-axis illumination systems, such as a colposcope, to improve the efficiency of the instrument.

It is another primary object of the present invention to provide an illumination system which adjustably allows projected light to be better guided to a viewing area of interest, with reduced shadowing, such as in the case of when swabs, probes, are used during a diagnostic inspection.

Therefore, and according to a preferred aspect of the present invention, there is provided an illumination beam director for use with a diagnostic instrument having means for illuminating and examining a target, the instrument having an optical lens system including a camera aperture for observing along an optical axis passing through the camera aperture, and an illuminator including an illuminator aperture for projecting illumination along a first illumination axis passing through the illumination aperture, the illumination director comprising:

first light redirecting means situated along the first illumination axis for receiving light from the illuminator and redirecting the light in a first direction;

second light redirecting means opposed to the first light redirecting means for receiving the redirected light from said first light redirecting means and redirecting the light along a second illumination axis, such that the second illumination axis is closer to the optical axis than is the first illumination axis at the first light redirecting means.

An advantage in using a beam director as taught by the present invention in combination with a colposcope as described, is that shadowing effects induced by the speculum or other sources extending into the viewing axis during examination are significantly reduced.

A further advantage is that the presently described beam director, can reduce shadowing without impacting the intensity of incident light projected on a particular target.

A further advantage is that the beam director can adjustably compensate for on-axis shadowing effects, as well as off-axis effects, to allow improved use of the viewing optics.

These and other advantages, objects, and features will now be described according to the following Detailed Description of the Invention, as illustrated by the accompanying drawings.

DETAILED DESCRIPTION OF THE INVENTION

The following discussion is directed to a preferred embodiment describing a colposcopic system for conducting a diagnostic medical examination of the cervix. It will be readily apparent, however, that the concepts described herein are also applicable to other diagnostic instruments, particularly those having off-axis illumination systems aligned relative to a viewing axis. In addition, terms such as "front", "rear", "top", "bottom", and "side" are used throughout the course of the discussion, but the use of these terms is to provide a frame of reference for reasons of clarity. These terms should not be limiting to the manner and form of possible embodiments covered by the appended claims.

Figure 1:
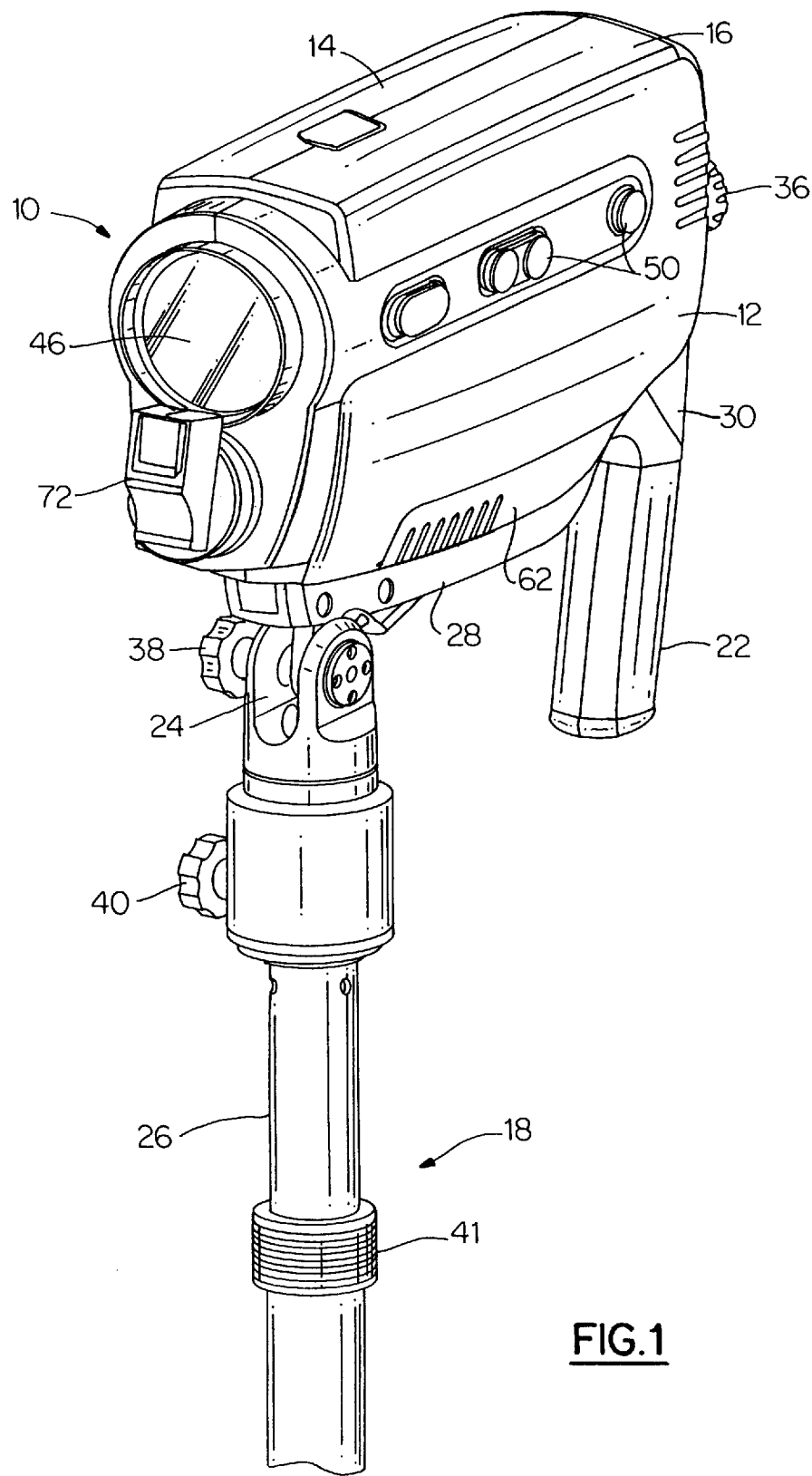
FIG. 1 is a partial front perspective view of a video colposcopic system according to the present invention.
Figure 2:
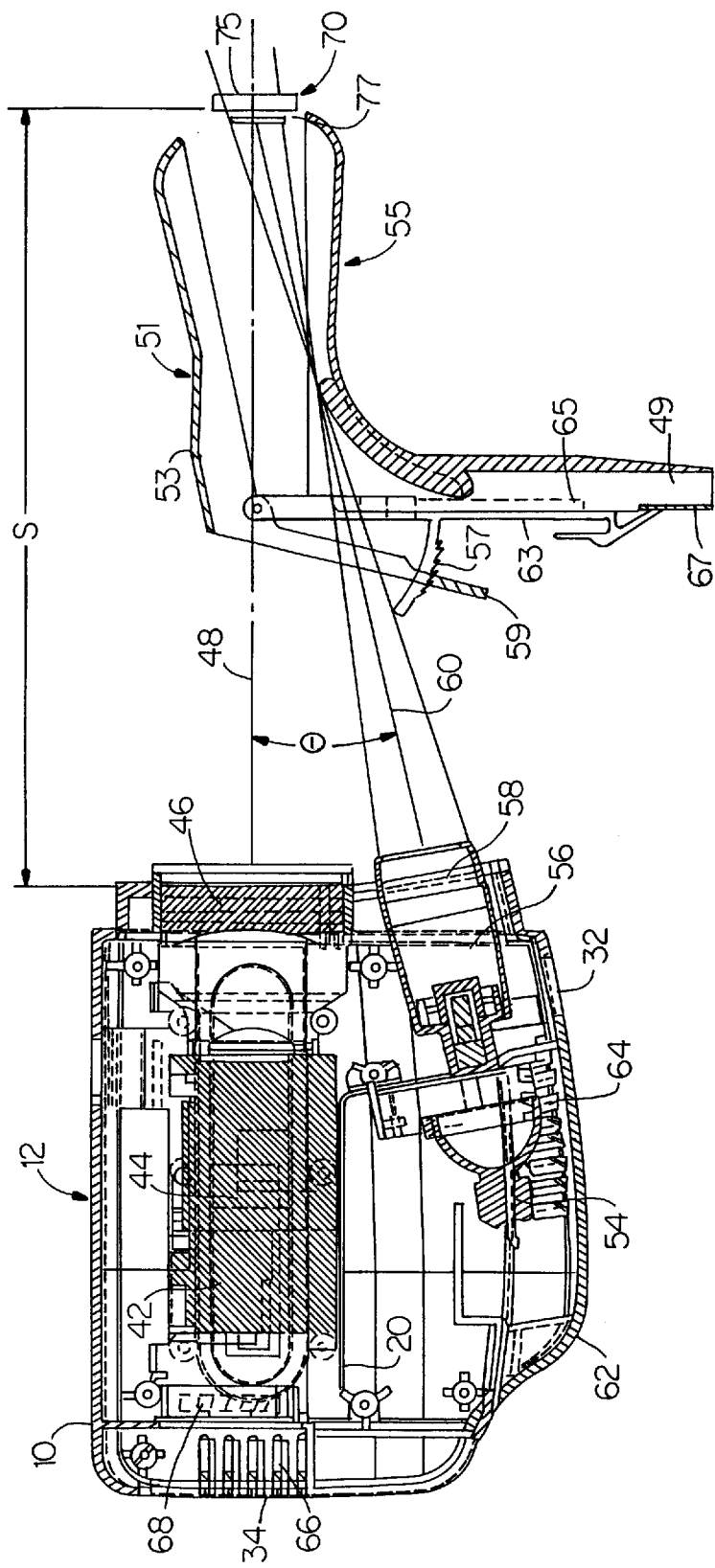
FIG. 2 is the side sectional view of the colposcope of FIG. 1 as used during an examination procedure.

As shown in FIGS. 1 and 2, there is provided a compact video colposcope 10 having a housing 12 made from a lightweight or other suitable material which is attached to a supporting fixture 18. The fixture 18 is not shown in FIG. 2, and is partially shown in FIG. 1. Preferably, the housing 12 includes a pair of half sections 14, 16 which sandwich a number of supported components therebetween, the components being supported on an internal casing 20. According to this embodiment, the supporting fixture 18 includes an interfacing handle portion 22, provided at the pivotal yoked end 24 of a vertical pole 26 extending from a base portion (not shown), and having respective bottom and side retaining portions 28, 30 sized for accommodating the bottom and rear sides 32, 34 of the housing 12 and attachable thereto by use of a locking knob 36. The supporting fixture 18 allows the colposcope 10 to be used in a variety of supported orientations by selective use of adjustment knobs 38, 40 and 41 in order to tip, rotate, and raise the attached instrument. Details relating to the attachment of the described colposcope 10 and the operation of the supporting fixture 18 are provided in commonly assigned and copending U.S. Ser. No. 08/748,375, the entire contents of which are hereby incorporated by reference.

According to the described embodiment, the colposcope 10 includes an optical system 42, including a video camera 44 and a series of linearly arranged optics, including a front facing optic or lens 46 which are housed within the upper portion of the housing 12 and define an optical axis 48. The video camera 44 contains a CCD imager to electronically capture and transmit a viewed image as is known in the art. According to the present embodiment, the video camera used is a SONY model-EVI-330 or 331.

The housing 12 includes a series of control switches 50 for controlling a motorized zooming mechanism (not shown), for focussing the optics which are set to focus nominally at approximately 250 mm–300 mm from the front lens 46, and for activating an electronic green filter (not shown) which removes a portion of the red color from the video image in order to promote vascular discrimination. The electronic green filter is described in greater detail in commonly assigned U.S. application Ser. No. 08/700,299, [Attorney Docket 282172] (Krauter, et al), filed Aug. 20, 1996.

The colposcope 10 also includes a self-contained illumination system which includes a light source, in this case a high intensity, subminiature arc lamp 54, which emits white light through a collimating tunnel 56 having an exiting aperture 58 for projecting illumination along a first illumination axis 60. The arc lamp 54 can be accessed through a removable portion or lamp door 62 of the housing 12 which is snap-fitted to the assembled half portions 14, 16. The lamp door 62 includes a spaced set of slit-like openings 64 for allowing heat to be dissipated from the housing 12, while a similar set of slit-like openings 66 are provided in the rear side 34 of the housing 12 in proximity to a cooling fan 68 disposed adjacent the video camera 44. The arc lamp 54 according to this embodiment is described in commonly assigned U.S. Pat. No. 5,083,059 (Graham, et al), the entire contents of which are hereby incorporated by reference.

As shown in FIG. 2, the illumination and optical axes 48, 60 converge at a target 70 (preferably the cervix, shown diagrammatically) located a predetermined distance (S) from the front optic 46, with an included angle θ therebetween. This position is coincidental with the approximate position of the cervix of a patient and preferably the focal point of the front optic 46. According to this embodiment, the angle θ is approximately 12 degrees.

According to this embodiment, the colposcope 10 includes a single electrical receptacle (not shown) in the rear of the housing 12 into which electrical connections are made with the components supported by the internal casing 20, including the video output of the video camera 44. The supporting fixture 18 on the other hand, includes a power supply (not shown) attached to the pole 26 and having a set of external ports (not shown) which allow electrical connection to an AC power input (not shown) and a series of peripheral devices, such as a video monitor (not shown) and a video printer (not shown). Each of these features are described in greater detail in co-pending and commonly assigned U.S. patent application Ser. No. 08/748,375, previously incorporated in its entirety.

As described by the Ser. No. 08/748,375 reference, the power supply (not shown) contains circuitry and cabling (not shown) extending through the interior of the pole 26 and channeled into the interfacing handle portion 22, and specifically into the electrical connector which then engages the rear electrical connector of the housing 12, when the colposcope is attached to the fixture 18. When a power switch (not shown) is activated on the rear of the interfacing handle portion 22, electrical power is applied to the colposcope components from the power supply (not shown) and the video output is transmitted through the engaged connectors to the power supply (not shown), and is then transmitted to the attached peripheral devices.

The interfacing handle portion 22 also includes a plurality of remote control buttons (not shown) for controlling the video image produced by the camera 44.

In use, the colposcope 10 is separably connectable to the interfacing handle portion 22 of the supporting fixture 18, or another supporting fixture (not shown) as described in the [Attorney Docket 281_240] reference.

Referring momentarily to FIG. 1, an illumination beam director 72 is shown, which is attached to the front of the housing 12 and over the exiting aperture 58, FIG. 2, of the light collimating tunnel 56, FIG. 2. The director 72 is not shown in FIG. 2 in order to better describe the normal working operation of the colposcope 10 as follows.

Therefore, referring specifically to FIG. 2, a speculum 51, of conventional design, is required for colposcopic examinations to hold the vaginal opening open to allow inspection of the cervix. The speculum 51 includes a pair of jaw-like molded plastic portions 53, 55 each having projecting ends which are introduced into the vaginal cavity (not shown). The lower jaw portion 55 is fixed relative to a base portion 49, while the upper jaw portion 53 is pivotally movable to open the vaginal cavity by means of a depending locking lever 59 which engages a set of radial locking tabs 57 that are a formed part of a yoke 63. This yoke 63 slides in a channel 65, shown in phantom, in the base portion 49. In use, the speculum 51 can be adjusted to a range of opening positions by selecting the proper locking tab 57, and ratchet step 67 on the base portion 49, thereby locking the upper jaw portion 53 into a fixed position.

The upper jaw portion 53 of the speculum 51 provides an opening which allows light to be freely transmitted without interruption between the target 70 and the video camera 44 along the optical axis 48. The presence of the base portion 49 and yoke 63, however, produces a partial shadow 75 and full shadow 77 on the target 70 due to the off-axis alignment of the illumination axis 60, darkening a portion of the target as perceived by the video camera 44. Illumination, of course, is necessary in order to adequately view the cervix visually.

Figure 3:
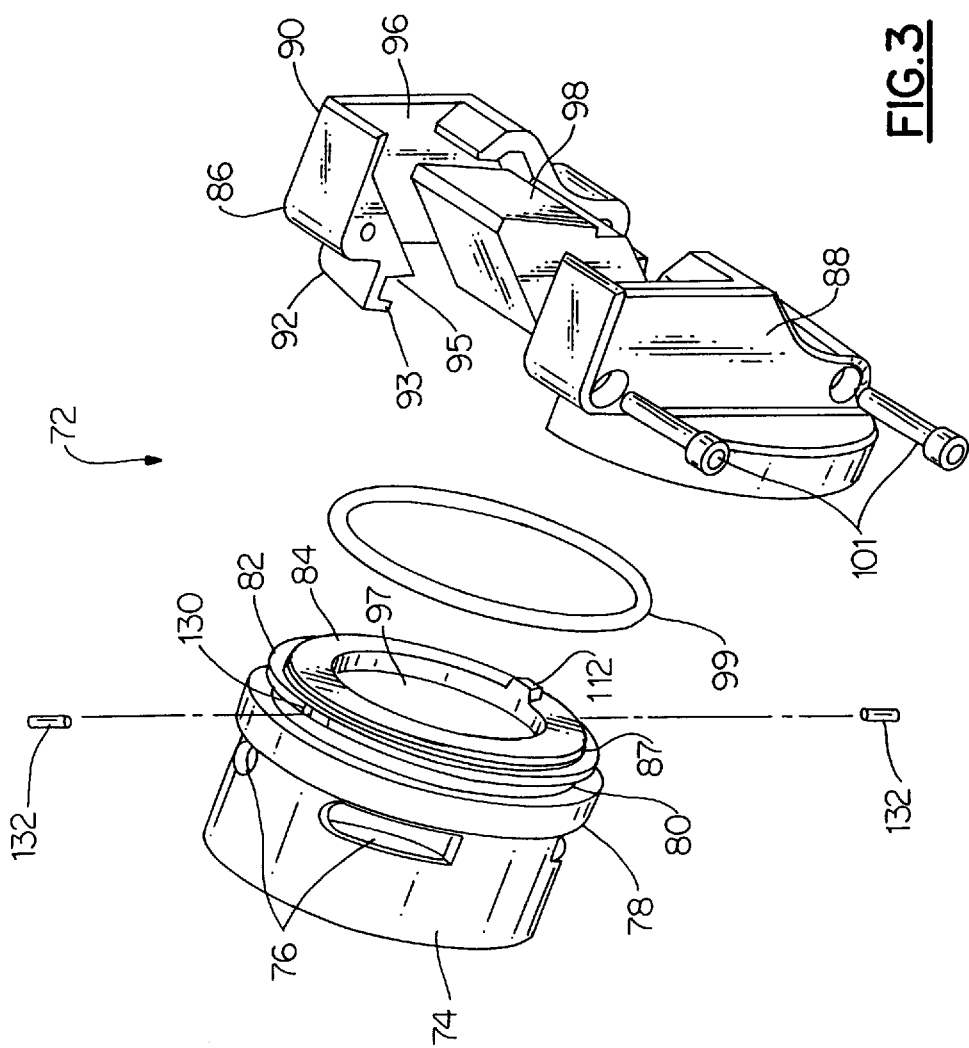
FIG. 3 is an exploded top perspective view of an illumination beam director for the colposcope shown in FIG. 1.
Figure 7:
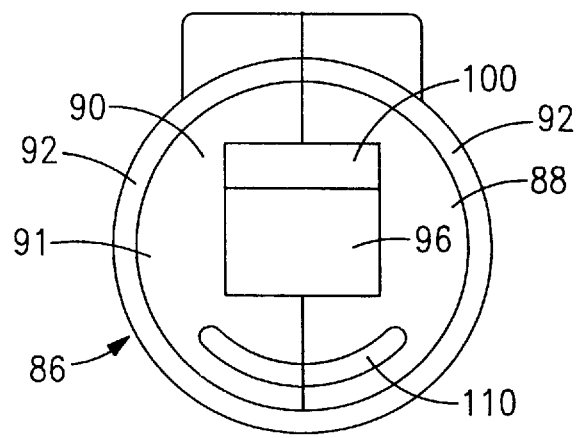
FIG. 7 is a partial rear view of a front movable portion of the illumination beam director of FIG. 3.
Figure 5:
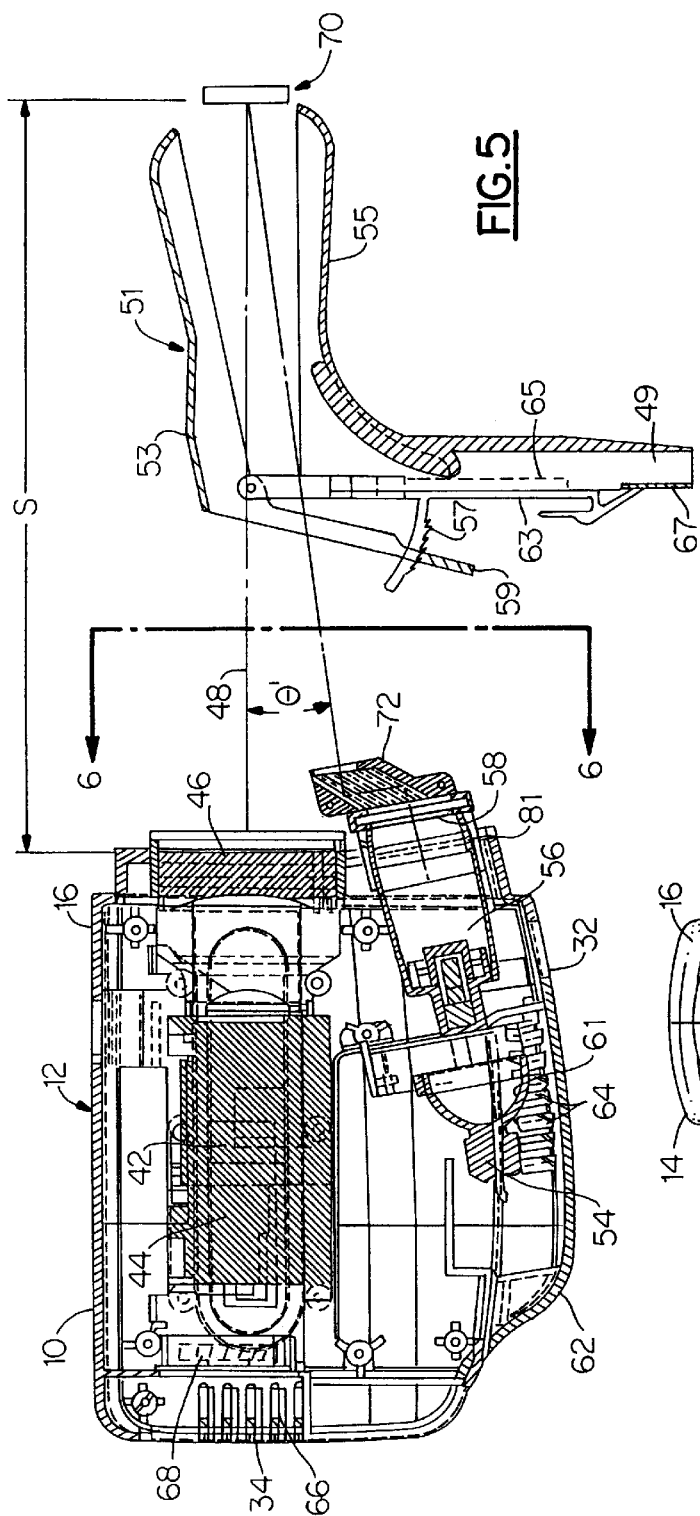
FIG. 5 is a side sectional view of the colposcope of FIG. 2, including the illumination director in accordance with a preferred embodiment of the invention.

Reference is now made to FIGS. 3, 5, and 7, in order to first describe the features of the illumination beam director 72, which includes a mounting barrel 74 having a cylindrical cross section and is sized for fitting over the light collimator tunnel 56. The mounting barrel 74 includes a series of slots 76 along the periphery of the barrel for engagement with tab sections 81 provided on the front ends of the housing sections 14, 16 which sandwich the director 72 therebetween, preferably during the assembly of the housing 12.

The beam director 72 also includes a front rotatable casing 86 assembled from a pair of interconnecting sections 88, 90 which define an interior 96 sized for retaining a light redirecting member 98, described in greater detail below, and including a pair of windows 100, 103, FIG. 6.

When assembled, the front casing 86 includes a ring-like circular rear engagement portion 92 for engaging a front engagement portion 78 of the mounting barrel 74. In particular, the front engagement portion 78 includes an annular groove 80 and adjacent radial engagement rib 82 for receiving an annular tab 93 and adjacent radial slot 95, respectively, of the rear engagement portion 92.

The front engagement portion 78 also includes a forward mounting surface 84 having a through aperture 97, the mounting surface having a projecting tab 112 extending therefrom for engaging a partial circumferential slot 110, FIG. 7, provided on a corresponding rearward mounting surface 91, FIG. 7, of the assembled front casing 86. A flexible O-ring 99 is also provided for fitting to the periphery 87 of the forward mounting surface 84 to provide means for damping when the front casing 86 is assembled. When assembled, the O-ring 99 also provides an axial load for the front of the annular tab 93 against the rear of the rib 82. In addition, the engagement rib 82 has a radial hole 130 provided at the top and at the bottom (not shown) of its rear surface. A pin 132 is then press fitted into each of these holes 130.

Figure 4:
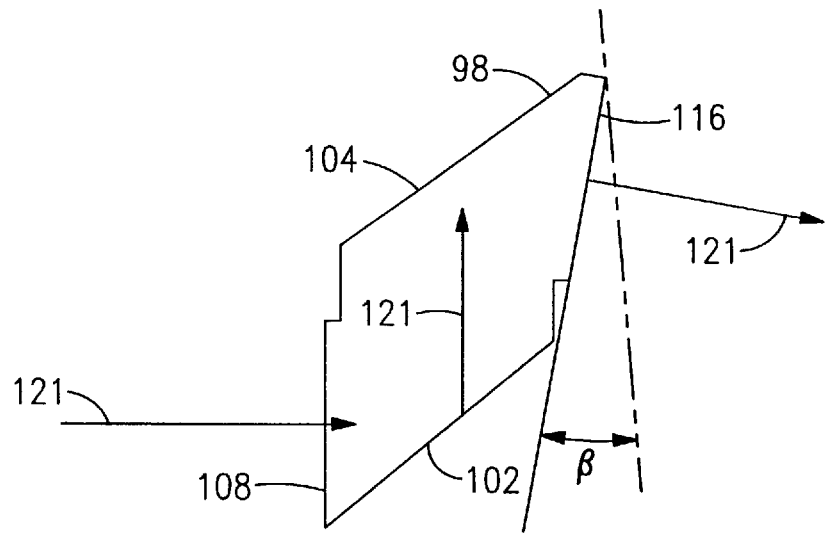
FIG. 4 is a side view of a light redirecting element contained in the illumination beam director of FIG. 3.

Referring to FIG. 4, the light redirecting member 98 is a prismatic element made of acrylic or other lightweight clear material and having a pair of angled surfaces 102, 104 which redirect the collimated light from the high intensity arc lamp 54 from the first illumination axis 60 to a second illumination axis 106.

In assembly, and referring to FIG. 3, the O-ring 99 is first placed over the forward mounting surface 84 and against a front facing surface of the radial engagement rib 82. The periphery 87 of the forward mounting surface 84 has a width dimension sized for retaining the O-ring 99.

One of the interconnecting sections 88, 90 is then aligned with the mounting barrel 74, and is fitted thereto by positioning the annular tab 93 and radial slot 95 of the rear engagement portion 92 of the section 88, 90 with the annular groove 80 and adjacent radial engagement rib 82 of the front engagement portion 78 of the mounting barrel 74.

The light redirecting member 98 is set into the defined interior 96 of the remaining section 90, 88 of the front casing 86 which is then similarly positioned to attach to the mounting barrel 74. The projecting tab 112 of the forward mounting surface 84 is engaged into the partial circumferential slot 110, FIG. 7, of the rearward mounting surface 91, FIG. 7, of the front casing 86. The casing 86 is fixedly attached by securing the sections 88,90 using threaded fasteners 101 to complete assembly of the director 72. Finally, the slots 76 of mounting barrel 74 are placed in the retaining tab portions 81 of the housing 12 for fitting the assembled director 72 to the colposcope housing 12.

Figure 6:
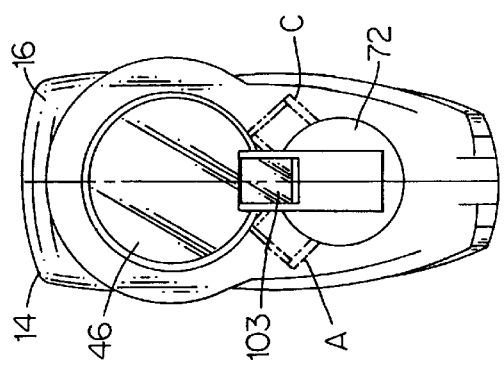
FIG. 6 is a partial front view of the colposcope and illumination beam director as viewed along the line 6—6 of FIG. 5.

Referring to FIGS. 3, 6 and 7, the O-ring 99 provides a frictional force in order to allow rotation of the front casing 86 about the periphery of the mounting barrel 74 after a predetermined mount of torque is applied, the rotation of the front casing being restricted by the partial circumferential slot 110. At the center rotational position of the casing 86, the pins 132 engage the split between the two sections 88, 90, thereby providing a detent feature as the casing is rotated between selected positions, as shown at extreme positions A and C in FIG. 6.

Referring now to FIGS. 3 and 5, the benefits of a colposcope 10 having the attached illumination beam director 72 is now apparent. As in the preceding discussion, a speculum 51 is used to hold open the vaginal cavity. In this instance, however, the presence of the beam director 72 causes light passing through the existing aperture 58 of collimator tunnel 56 to also pass through aperture 97 of the mounting barrel 74. As most particularly shown in FIGS. 5–7, the illumination beam director 72 can be rotated within the range dictated by the engagement of the projecting rib 112 within the partial circumferential slot 110. In the detent or center position, the light, shown as arrow 121, FIG. 4, passes through an entrance surface 108 of the prismatic member 98, is intercepted by the lower redirecting surface 102 and is reflected upwardly toward the opposite second redirecting surface 104. Each of the redirecting surfaces 102, 104 has a reflective or mirrored exterior coating in order to insure that the light reflects therefrom. The light is finally redirected through an exit surface 116 and the window 103 along a second illumination axis 106 which is closer to the optical axis 48 than is the first illumination axis 60. The angle ($\theta'$) between the second illumination axis 106 and the optical axis 48 is about 7 degrees. The redirected light does not significantly degrade in intensity and provides sufficient illumination without shadowing of the speculum 51 onto the cervix. In this position of the front casing 86, the axis of the redirected light is in the plane defined by the axes 48, 60. Rotation of the casing 86 about the first illumination axis 60 from the detent position (see positions A and C, FIG. 6), causes the axis of the redirected light to shift laterally out of this plane. The illumination can thereby pass by an instrument or other object (not shown) which is inserted into the vaginal cavity so as to additionally minimize any shadowing effects which might be produced.

In addition and as clearly shown in FIG. 4, at least one of the exit and entrance surfaces 108, 116 are angled ($\beta$) in order to allow the redirected light to be projected to the same convergence point shown in FIGS. 2 and 5, despite the change in the included angle $\theta \rightarrow \theta'$ between the optical and illumination axes 48, 106. For purposes of this embodiment, a suitable angle ($\beta$) is about 5 degrees.

PARTS LIST FOR FIGS. 1–7

10 compact colposcope
12 housing
14 half section
16 half-section
18 supporting fixture
20 internal casing
22 interfacing handle portion
24 yoked end
26 vertical pole
28 bottom retaining portion
30 side retaining portion
32 bottom side of housing
34 rear side of housing
36 locking knob
38 adjustment knob
40 adjustment knob
41 adjustment knob
42 optical system
44 video camera
46 front optic
48 optical axis
49 base portion
50 remote control switches
51 speculum
52 illumination system
53 upper jaw portion
54 arc lamp
55 lower jaw portion
56 light collimating tunnel 57 radial locking tabs
58 exiting aperture
59 locking lever
60 first illumination axis
62 lamp door
63 yoke
64 slit-like openings
65 channel
66 slit-like openings
67 ratchet steps
68 cooling fan
70 target
72 illumination beam director
74 mounting barrel
75 partial shadow
76 peripheral slots
77 fall shadow
78 front engagement portion
80 annular groove
81 tab sections-housing
82 radial engagement rib
84 forward mounting surface
86 front casing
87 periphery
88 interconnecting section
90 interconnecting section
91 rearward mounting surface
92 rear engagement portion
93 annular tab
95 radial slot
96 interior
97 through aperture
98 light redirecting member
99 O-ring
100 window
101 threaded fasteners
102 lower light redirecting surface
104 upper light redirecting surface
106 second illumination axis
108 entrance surface
110 circumferential slot
112 projecting tab
116 exit surface
121 arrow
130 radial holes
132 pins While the invention has been described with reference to a preferred embodiment, it will be appreciated that various modifications can be made without departing from the spirit of the invention. Such modifications are intended to fall within the scope of the appended claims.

We claim:

1. A diagnostic instrument comprising:
a housing;
an optical system disposed within said housing;
an illumination system adjacently disposed relative to said optical system, said optical system having at least one optical element and a viewing aperture for defining an optical axis for viewing a target, said illumination system including a light source and an illumination aperture defining an illumination axis to allow illumination to be projected onto said target, wherein said illumination and said optical axes converge only at a single point from said diagnostic instrument onto said target disposed a predetermined distance from said housing, said axes having an included angle therebetween, and;
means for redirecting at least one of said optical and illumination axes to reduce said angle without changing the single converging point of said axes;
wherein said redirecting means are disposed at an intermediate location along one of said axes.

2. A diagnostic instrument as recited in claim 1, wherein said axis redirecting means includes a beam directing element having first light redirecting means disposed along an initial illuminating axis to redirect light in a first direction and second light redirecting means for receiving and redirecting the light along a second illumination axis wherein said second illumination axis forms a smaller angle with said optical axis than said initial illuminating axis.

3. A diagnostic instrument as recited in claim 2, wherein said beam directing element includes a housing having a prismatic element disposed therein, said prismatic element including a pair of opposing light redirecting surfaces, in which a first redirecting surface is disposed in said first illumination axis for redirecting light from said light source in said first direction, and a second light redirecting surface is substantially opposed to said first light redirecting axis for receiving and redirecting said light along said second illumination axis.

4. A diagnostic instrument as recited in claim 3, wherein at least one of said first and second light redirecting surfaces is angled relative to the first illumination axis for redirecting the light along the second illumination axis without changing the predetermined distance at which said optical and first illumination axes converge.

5. A diagnostic instrument as recited in claim 2, wherein said beam directing element includes means for rotatably attaching to said illumination system to allow rotation of said element about said first illumination axis.

6. A diagnostic instrument as recited in claim 5, wherein said beam director element includes a mounting section for attaching to said housing, and an adjustable section mounted for rotation on said mounting section, said prismatic member being included in said adjustable section.

7. A diagnostic instrument as recited in claim 6, including means for restricting rotational movement of said adjustable section within a predetermined range of positions.

8. A diagnostic instrument as recited in claim 7, wherein said rotational restriction means includes a circumferential slot disposed on either of said mounting section and said adjustable section for engagement by a tab disposed on the other of said mounting and adjustable sections.

9. A diagnostic instrument as recited in claim 8, including detent means for indicating when said adjustable section has been rotated to a centered position relative to said mounting portion.

10. A diagnostic instrument as recited in claim 6 including damping means for preventing the adjustable portion from rotating until a predetermined amount of torque is exceeded.

11. A diagnostic instrument as recited in claim 10, wherein said damping means includes an O-ring disposed between contact surfaces of said adjustable section and said mounting section.

12. A diagnostic instrument as recited in claim 11, wherein said instrument is a colposcope, in which said adjustable section allows redirected light along said second illumination axis to be selectively shifted laterally relative to said optical axis to avoid shadowing of instruments placed in relation to the target.

13. A diagnostic instrument as recited in claim 12, wherein said illumination system of said colposcope is disposed below said optical system.

14. A diagnostic instrument as recited in claim 13, wherein said illumination system is disposed above said optical system.

* * * * *